United States Patent [19]

Szántay et al.

[11] 4,356,305
[45] Oct. 26, 1982

[54] PROCESS FOR THE PREPARATION OF HALOVINCAMONE DERIVATIVES

[75] Inventors: Csaba Szántay; Lajos Szabó; György Kalaus; Lajos Dancsi; Tibor Keve; Ferenc Drexler, all of Budapest, Hungary

[73] Assignee: Richter Gedeon Vegyeszeti Gyar Rt., Budapest, Hungary

[21] Appl. No.: 175,384

[22] Filed: Aug. 5, 1980

[30] Foreign Application Priority Data

Aug. 13, 1979 [HU] Hungary .................. RI 722

[51] Int. Cl.³ .................. C07D 461/00; A61K 31/435
[52] U.S. Cl. ......................... 546/51; 424/251
[58] Field of Search ............. 546/51; 424/256

[56] References Cited

U.S. PATENT DOCUMENTS

| | | | |
|---|---|---|---|
| 3,852,453 | 12/1974 | Giudicelli et al. | 424/256 X |
| 4,045,443 | 8/1977 | Pfäffli | 546/51 |
| 4,146,643 | 3/1979 | Pfäffli | 546/51 X |
| 4,190,658 | 2/1980 | Warnant et al. | 424/256 |
| 4,283,401 | 8/1981 | Szántay et al. | 424/256 |
| 4,285,865 | 8/1981 | Szántay et al. | 424/256 X |
| 4,285,949 | 8/1981 | Hannart | 424/256 |
| 4,285,950 | 8/1981 | Szántay et al. | 424/256 |

FOREIGN PATENT DOCUMENTS

| | | | |
|---|---|---|---|
| 1940 | 5/1979 | European Pat. Off. | 546/51 |
| 2703920 | 8/1977 | Fed. Rep. of Germany | 546/51 |
| 2085630 | 12/1971 | France | 424/256 |
| 2339618 | 9/1977 | France | 546/51 |

OTHER PUBLICATIONS

Szántay et al., Chemical Abstracts, vol. 88, 51061v, (1978).
Gibson et al., Chemical Abstracts, vol. 71, 81593m, (1969).
Lewin et al., Heterocycles, vol. 14, No. 12, pp. 1915-1920, (12/80).

Primary Examiner—Donald G. Daus
Assistant Examiner—Diana G. Rivers
Attorney, Agent, or Firm—Karl F. Ross

[57] ABSTRACT

The invention relates to new halovincamone derivatives of the general formula (I),

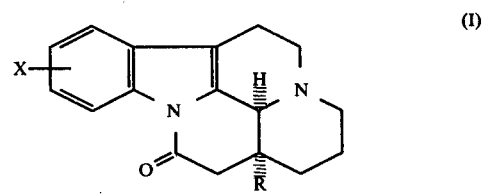

wherein R is a $C_{1-6}$ alkyl group and X is halogen, and pharmaceutically acceptable acid addition salts and optically active isomers thereof. These compounds possess valuable vasodilating effect, and can be applied to advantage in the therapy.

The new compounds defined above are prepared according to the invention so that a single epimer or an epimeric mixture of a racemic or optically active halogenated 14-oxo-15-hydroxy-E-homoeburnane derivative of the general formula (II),

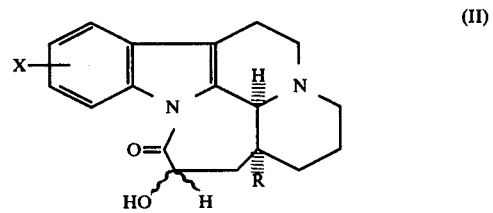

wherein R and X are as defined above, or an acid addition salt thereof is treated with an oxidizing agent, and, if desired, the resulting compound of the general formula (I) is converted into its pharmaceutically acceptable acid addition salt and/or resolved.

1 Claim, No Drawings

PROCESS FOR THE PREPARATION OF HALOVINCAMONE DERIVATIVES

The invention relates to new halovincamone derivatives of the formula (I),

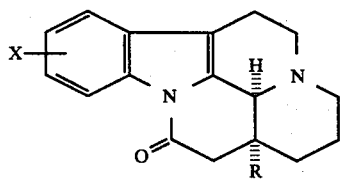

(I)

wherein R is a $C_{1-6}$ alkyl group and X is halogen, and pharmaceutically acceptable acid addition salts and optically active isomers thereof.

The invention also relates to pharmaceutical compositions which contain at least one of the new compounds defined above, furthermore to a process for the preparation of the new compounds and the pharmaceutical compositions.

The new compounds defined above are prepared according to the invention so that a single epimer or an epimeric mixture of a racemic or optically active halogenated 14-oxo-15-hydroxy-E-homoeburnane derivative of the formula (II),

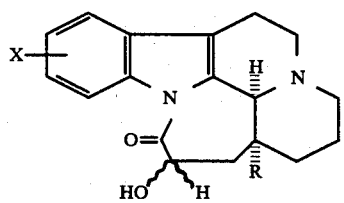

(II)

wherein R and X are as defined above, or an acid addition salt thereof is treated with an oxidizing agent, and, if desired, the resulting compound of the general formula (I) is converted into its pharmaceutically acceptable acid addition salt and/or resolved.

The new compounds according to the invention possess valuable vasodilating effects.

In the compounds of the formulae (I) and (II) R can represent a straight-chained or branched $C_{1-6}$ alkyl group, such as methyl, ethyl, n-propyl, isopropyl, n-butyl, sec.-butyl, ter.-butyl, n-pentyl, isopentyl, n-hexyl or isohexyl group. R is preferably an ethyl or n-butyl group.

X may represent any of the four halogens, i.e. fluorine, chlorine, bromine and iodine, preferably bromine.

In the compounds of the general formula (I) X may be attached to any of the carbon atoms of the benzene ring. Of the structural isomers the 9, 10 and 11-halovincamone derivatives are preferred.

The starting substances of the formula (II) in which substituent X is attached to position 9 or 11 of the ring system can be prepared by the direct halogenation of the respective unsubstituted 14-oxo-15-hydroxy-E-homoeburnane derivative. This process is described in detail in our co-pending Hungarian patent application No. RI-721.

The starting substances of the general formula (II) in which substituent X is attached to position 10 of the ring system can be prepared by subjecting the respective 9-halo-1-(2-hydroxy-2-alkoxycarbonylethyl)-octahydroindolo[2,3-a]quinolisine to alkaline treatment. Further details of this method can be found in our co-pending Hungarian patent application No. RI-723.

Active oxidizing agents, preferably active manganese dioxide, precipitated onto an inert support with large surface area, such as celite, can be used as reactants in the process of the invention (see Tetrahedron 33, 1803).

The starting substances of the formula (II) are oxidized in an inert aprotic non-polar organic solvent, such as an aliphatic hydrocarbon, halogenated aliphatic hydrocarbon (e.g. chloroform, dichloromethane, dichloroethane, etc.), aromatic hydrocarbon (e.g. toluene, xylene, etc.) or cyclic ether (e.g. dioxane, tetrahydrofuran, etc.).

Oxidation is performed at temperatures above room temperature, such as at 40° to 140° C. It is preferred to operate at the boiling point of the solvent applied.

The compounds of the formula (I) can be reacted with various acids to form the respective pharmaceutically acceptable acid addition salts. Of the acids applicable in the salt formation step, e.g. the following are to be mentioned: mineral acids, such as hydrogen halides (e.g. hydrochloric acid and hydrogen bromide), sulfuric acid, phosphoric acid, nitric acid, perhaloic acids (e.g. perchloric acid), etc., organic carboxylic acids, such as formic acid, acetic acid, propionic acid, glycolic acid, maleic acid, hydroxymaleic acid, fumaric acid, tartaric acid, succinic acid, ascorbic acid, citric acid, maleic acid, salicylic acid, lactic acid, cinnamic acid, benzoic acid, phenylacetic acid, p-aminobenzoic acid, p-hydroxybenzoic acid, p-aminosalicyclic acid, etc., alkylsulfonic acids, such as methanesulfonic acid, ethanesulfonic acid, etc., cycloaliphatic sulfonic acids, such as cyclohexylsulfonic acid, arylsulfonic acids, such as p-toluenesulfonic acid, naphthylsulfonic acid, sulfanylic acid, etc., amino acids, such as aspartic acid, glutamic acid, N-acetylaspartic acid, N-acetylglutamic acid, etc.

Salt formation can be performed in an inert organic solvent, such as a $C_{1-6}$ aliphatic alcohol, so that the racemic or optically active compound of the formula (I) is dissolved in the solvent, and the selected acid or a solution thereof formed with the same solvent is added to the solution of the base until the latter becomes slightly acidic (pH 5-6). The precipitated acid addition salt can be separated from the reaction mixture e.g. by filtration.

The racemic compounds of the formula (I) can be resolved in a manner known per se to obtain the respective optically active derivatives. The optically active end-products can also be prepared, however, from the appropriate optically active starting substances.

If desired, the racemic or optically active compounds of the formula (I), as well as the acid addition salts thereof can be subjected to further purification steps, such as recrystallization from an appropriately selected solvent or solvent mixture. The solvents or solvent mixtures utilized in this step are selected in accordance with the solubility and crystallization characteristics of the substance to be purified. $C_{1-6}$ aliphatic alcohols, acetonitrile and related solvents can be used to advantage as recrystallizing agents.

The process of the invention yields the end-products in forms easy to identify. The IR spectra and mass spectra of the compounds prepared are in harmony with the assigned structures.

The compounds of the formula (I) were subjected to pharmacological tests in order to determine their effects on the circulation.

The tests were performed on dogs narcotized with chloralose urethane, and the arterial blood pressure, heart rate, and the blood flows in the femoral artery and internal carotid artery were measured. Vascular resistances were calculated for the latter two vascular beds by the formula $$\text{vascular resistance} = \frac{\text{blood pressure}}{\text{blood flow}}.$$

The substances under examination were administered as aqueous solutions in intravenous doses of 1 mg/kg body weight. The tests were repeated five or six times. The results of the tests are listed in Table 1, whereas the corresponding properties of vincamine (reference substance) are given in Table 2.

TABLE 1

Circulation effects of 10-bromovincamone-(3α,16α) (mean values ± standard error)

| | Control | Treated | Percentage difference |
|---|---|---|---|
| MABP | 145 ± 5.9 | 140 ± 7.1 | −3.4 |
| HR | 157 ± 15 | 154 ± 16 | −1.9 |
| CBF | 65.2 ± 15 | 75.8 ± 14 | +16 |
| CVR | 2.22 ± 0.36 | 1.85 ± 0.17 | −17 |
| FBF | 40.4 ± 11 | 40.8 ± 11 | +1.0 |
| FVR | 3.59 ± 0.52 | 3.43 ± 0.49 | −4.5 |

TABLE 2

Circulation effects of vincamine (mean values ± standard error)

| | Control | Treated | Percentage difference |
|---|---|---|---|
| MABP | 131 ± 5.2 | 112 ± 6.1 | −15 |
| HR | 181 ± 19 | 165 ± 15 | −9.1 |
| CBF | 39.2 ± 8.6 | 40.8 ± 8.5 | +4.1 |
| CVR | 3.35 ± 0.56 | 2.74 ± 0.52 | −18 |
| FBF | 35.9 ± 7.2 | 42.8 ± 7.4 | +19 |
| FVR | 3.65 ± 0.58 | 2.61 ± 0.53 | −28 |

The abbreviations used in the tables have the following meanings:
MABP: mean arterial blood pressure (mm Hg)
HR: heart rate (min$^{-1}$)
CBF: internal carotid blood flow (ml.min$^{-1}$)
CVR: carotid vascular resistance (mm Hg.min.ml$^{-1}$)
FBF: femoral blood flow (ml.min$^{-1}$)
FVR: femoral vascular resistance (mm Hg.min.ml$^{-1}$)

The data of the tables indicate that 10-bromovincamone-(3α,17α) hardly affects the blood pressure and the heart rate when administered to narcotized dogs in an intravenous dose of 1 mg/kg body weight, i.e. it exerts favorably weak effects on the systemic circulation. The main effect of 10-bromovincamone-(3α,17α) is the dilatation of the carotid artery, which may reach 17%, corresponding to a 16% increase in blood flow. It is particularly advantageous that this compound exerts practically no other effect on the circulation.

Owing to their flavoring vasodilating effects, the new compounds according to the invention can be used to advantage in therapy.

The new compounds according to the invention can be converted into pharmaceutical compositions for parenteral or enteral administration, utilizing conventional non-toxic, inert, solid or liquid pharmaceutical carriers, diluents and/or auxiliary agents. As carrier e.g. water, gelatine, lactose, starch, pectin, magnesium stearate, stearic acid, talc and vegetable oils such as peanut oil, olive oil, etc. can be applied. The pharmaceutical compositions can be presented in conventional forms, e.g. as solids (round or angular tablets, coated tablets, capsules, such as hard gelatine capsules, furthermore pills, suppositories, etc.) or liquids (such as oily or aqueous solutions, suspensions, emulsions, syrups, soft gelatine capsules, injectable oily or aqueous solutions or suspensions, etc.). The amount of the solid carrier present may vary within wide limits; the solid compositions may contain preferably about 25 mg to 1 g of a carrier. If necessary, the pharmaceutical compositions may also contain conventional pharmaceutical additives, such as preservatives, wetting agents, emulsifying agents, salts for adjusting the osmotic pressure, buffers, flavoring agents, odorants, etc. If desired, the compositions may also contain other known pharmaceutically active substances in addition to the new compounds according to the invention. The pharmaceutical compositions are presented preferably in the form of unit dosages corresponding to the way of administration. The pharmaceutical compositions are prepared by methods well known in the pharmaceutical industry, such as sieving, mixing, granulating and pressing the components, dissolving the substances, etc. If desired, the compositions can also be subjected to other conventional pharmacotechnological operations, such as sterilization.

The invention is elucidated in detail by the aid of the following non-limiting Examples.

EXAMPLE 1

10-Bromovincamone-(3α,16α)

10.7 g of active manganese dioxide precipitated onto celite support are added to a solution of 0.65 g (1.6 mmoles) of 10-bromo-14-oxo-15-hydroxy-E-homoeburnane-(3α,17α) in 50 ml of dry dichloromethane, and the resulting mixture is refluxed for 5 hours under constant stirring. The suspension is allowed to cool, the solids are filtered off, washed with dry dichloromethane, and the wash is combined with the filtrate. This solution is evaporated to dryness in vacuo, and the solid residue is crystallized from 10 ml of methanol.

0.40 g (61.8%) of the title compound are obtained as a white, crystalline substance melting at 191°–192° C. The empirical formula of the product is $C_{19}H_{21}BrN_2O$ (mol. wt.: 373.3).

IR spectrum (KBr): $\nu_{max}$. 1710 cm$^{-1}$ (amide CO).

Mass spectrum (m/e): 374, 373, 372, 371, 317, 315, 304, 302, 293, 264, 260, 258, 195, 180, 139, 41.

EXAMPLE 2

9-Bromovincamone-(3α,17α)

3 g of active manganese dioxide precipitated onto celite support are added to a solution of 0.21 g (0.52 mmoles) of 9-bromo-15-hydroxy-14-oxo-E-homoeburnane-(3α,17α) in 20 ml of dry dichloromethane, and the resulting suspension is refluxed for 5 hours under constant stirring. The suspension is allowed to cool, the solids are filtered off, and washed thrice with 5 ml of dry dichloromethane, each. The wash and the filtrate are combined, evaporated to dryness in vacuo, and the solid residue is crystallized from 5 ml of methanol. 0.083 g (42.7%) of the title compound are obtained as a crystalline solid melting at 188°–189° C. The empirical formula of the product is $C_{19}H_{21}BrN_2O$ (mol. wt.: 373.3).

IR spectrum (KBr): $\nu_{max}$. 1700 cm$^{-1}$ (amide CO).

EXAMPLE 3

11-Bromovincamone-(3α,17α)

10 g of active manganese dioxide precipitated onto celite support are added to a solution of 0.668 g (1.66 mmoles) of 11-bromo-15-hydroxy-14-oxo-E-homoeburnane-(3α,17α) in 70 ml of dichloromethane, and the resulting suspension is refluxed for 5 hours under constant stirring. The suspension is allowed to cool, the solids are filtered off and washed thrice with 15 ml of dry dichloromethane, each. The filtrate and the wash are combined, evaporated to dryness in vacuo, and the solid residue is crystallized from 10 ml of methanol. 0.3 g (48.5%) of the title compound are obtained as a crystalline solid melting at 207°–209° C. The empirical formula of the product is $C_{19}H_{21}BrN_2O$ (mol. wt.: 373.3).

IR spectrum (KBr): $\nu_{max}$. 1695 cm$^{-1}$ (amide CO).

EXAMPLE 4

(−)-11-Bromovincamone-(3α,16α)

6.0 g of active manganese dioxide precipitated onto celite support are added to a solution of 0.4 g (0.99 mmoles) of (+)-11-bromo-14-oxo-15-hydroxy-E-homoeburnane-(3α,17α) in 40 ml of dry dichloromethane, and the reaction mixture is refluxed for 3 hours under constant stirring. The suspension is allowed to cool, the solids are filtered off, washed thrice with 10 ml of dry dichloromethane, each, and the filtrate is combined with the wash. The resulting solution is evaporated to dryness in vacuo, and the oily residue, weighing 0.35 g, is crystallized from 5 ml of acetonitrile. 0.182 g (49.2%) of the title compound are obtained as a crystalline solid melting at 162°–164° C.

IR spectrum (KBr): $\nu_{max}$. 1710 cm$^{-1}$ (amide CO).
$[\alpha]_D^{25} = -96.2°$ (c=1%, in chloroform).

EXAMPLE 5

(−)-9-Bromovincamone-(3α,16α)

3.0 g of active manganese dioxide precipitated onto celite support are added to a solution of 0.2 g (0.49 mmoles) of (+)-9-bromo-14-oxo-15-hydroxy-E-homoeburnane-(3α,17α) in 20 ml of dry dichloromethane, and the suspension is refluxed for 3 hours under constant stirring. The reaction mixture is allowed to cool, the solids are filtered off, and washed thrice with 5 ml of dry dichloromethane, each. The filtrate and the wash was combined, evaporated to dryness in vacuo, and the 0.15 g of oily residue are crystallized from 3 ml of acetonitrile. 0.09 g (48.6%) of the title compound are obtained as a crystalline substance melting at 185°–187° C. The empirical formula of the product is $C_{19}H_{21}BrN_2O$ (mol. wt.: 373.30).

IR spectrum (KBr): $\nu_{max}$. 1695 cm$^{-1}$ (amide CO).
$[\alpha]_D^{25} = -14.8°$ (c=1%, in chloroform).

PREPARATION OF THE STARTING MATERIALS OF THE FORMULA (II)

The starting materials of the formula (II) where X is halogen in the 9- or 11-position of the 14-oxo-15-hydroxy-E-homoeburnane are prepared themselves by treating a racemic or optically active 15-hydroxy-E-homoeburnane of the formula (III)

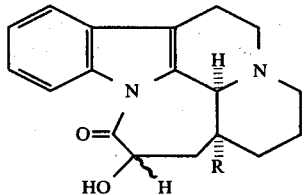

(III)

wherein R is as defined above, or a pharmaceutically acceptable acid addition salt thereof, with a halogenating agent. The particular isomers with the 9-halo- and 11-halo- substituents of the formula (II) may be separated from one another, and then any of the compounds is converted into the pharmaceutically acceptable acid addition salt and/or resolved, if desired.

The racemic or optically active 15-hydroxy-E-homoeburnanes of the formula (III) can be prepared by the method described in Tetrahedron 33, 1803 (1977).

The 15-hydroxy-E-homoeburnanes of the formula (III) are halogenated with reactants capable of introducing a halogen atom into the unsaturated ring without simultaneously replacing the 15-hydroxy group by a halogen. It is preferred to use elemental halogens as the halogenating agents.

According to a preferred method, compounds of the formula (II) where X is bromo in the 9- or 11-position are prepared. The corresponding starting substances of the formula (III) are brominated, preferably, with elemental bromine, but other brominating agents leading to the formation of the required bromo-compounds may be used.

Bromination is performed in an inert, organic solvent or solvent mixture. Of the solvents usable in this step, the following are to be mentioned: non-polar organic solvents, such as halogenated aliphatic hydrocarbons (e.g. chloroform, dichloromethane, dichloroethane), furthermore polar organic solvents, such as organic acids (e.g. glacial acetic acid, propionic acid).

In some instances it is preferred to perform bromination in the presence of a Lewis acid. As the Lewis acid, e.g. ferric chloride, zinc chloride, aluminum chloride, stannic chloride, antimony tetrachloride or boron trifluoride may be used.

Bromination can be performed at temperatures of 20° C. to 40° C., preferably at room temperature.

The ratio of the stereoisomers formed in the reaction depends on the rate of the bromine administration.

When brominating a compounds of the formula (III), a mixture of the 9-bromo and 11-bromo compounds of the formula (II) is obtained. The two stereoisomer bromine derivatives can be separated from one another by methods known per se, such as crystallization, salt formation and separation, or preparative layer chromatography. It is preferred to use Merck PF 254+366 grade silica gel as adsorbent in the preparative layer chromatography. Various solvent combinations can be utilized as running and eluting agents.

PREPARATION EXAMPLE 1

(±)-9-Bromo-14-oxo-16-hydroxy-E-homoeburnane-(3α,17α) and (±)-11-bromo-14-oxo-16-hydroxy-E-homoeburnane-(3α,17α)

(a) 1.1 g of ferric chloride hexahydrate are added to a solution of 1.30 g (4.01 mmoles) of (±)-14-oxo-15- hydroxy-E-homoeburnane-(3α, 17α), melting at 193° C. to 195° C., in 15 ml of glacial acetic acid, and 5 ml of a 1 molar bromine solution in glacial acetic acid are added dropwise to the mixture at room temperature under constant stirring. The bromine solution is introduced slowly, at a rate of 0.5 ml/min. When the addition is complete the mixture is stirred for additional 9 hours at room temperature. When the reaction terminates 200 ml of water are added to the suspension, and the pH of the resulting mixture is adjusted to 5 with 25% aqueous ammonia. The mixture is extracted with 100, 80 and 60 ml of dichloromethane. The organic solutions are combined, admixed with 100 ml of water, and the pH of the mixture is adjusted to 10 with 25% aqueous ammonia. The two-phase mixture is shaken, thereafter the dichloromethane phase is separated, washed thrice with 100 ml of water, each, dried over anhydrous solid magnesium sulfate, filtered, and the filtrate is evaporated to dryness in vacuo.

The 1.4 g of dry residue obtained are subjected to preparative thin layer chromatography. Kieselgel PF$_{254+366}$ grade silica gel plates, 20×20 cm in area and 1.5 mm in thickness, are applied as adsorbent, and a 10:3 mixture of benzene and acetonitrile is applied as solvent. The eluted substances are crystallized from methanol. 0.15 g (11%) of (±)-9-bromo-14-oxo-15-hydroxy-E-homoeburnane-(3α,17α) are isolated from the upper spot. The substance melts at 202° C. to 203° C. The empirical formula of the product is $C_{20}H_{23}BrN_2O_2$ (mol. wt.: 403.33).

IR spectrum (KBr): $v_{max}$. 3410 cm$^{-1}$ (—OH), 1685 cm$^{-1}$ (amide —CO).

NMR spectrum (deuterochloroform): δ=0.97 (t, 3H, CH$_3$), 7.21-8.64 (m, 3H, aromatic protons).

$C_{10}$—H=7.51 ppm, $J_{11,12}$=7.8 Hz (ortho)
$C_{11}$—H=7.21 ppm, $J_{11,10}$=7.6 Hz (ortho)
$C_{12}$—H=8.64 ppm, $J_{10,12}$=1.9 Hz (meta).

Mass spectrum (m/e): 404, 403, 402, 401, 376, 374, 360, 358, 347, 345, 332, 330, 317, 315, 303, 301, 277, 275, 180, 167, 153, 140.

0.63 1 g (46.1%) of (±)-11-bromo-14-oxo-15-hydroxy-E-homoeburnane-(3α,17α) are isolated from the middle spot. The substance melts at 195° C. to 197° C. The empirical formula of the product is $C_{20}H_{23}BrN_2O_2$ (mol. wt.: 403.33).

IR spectrum (KBr): $v_{max}$. 3350 cm$^{-1}$ (—OH), 1680 1 cm$^{-1}$ (amide —CO).

NMR spectrum (deuterochloroform): δ=0.95 1 (t, 3H, CH$_3$), 7.25-8.69 (m, 3H, aromatic protons) ppm.

$C_9$—H=7.25 ppm, $J_{10,12}$=1.9 Hz (meta)
$C_{10}$—H=7.39 ppm, $J_{10,9}$=7.7 Hz (ortho) $C_{12}$—H=8.69 ppm, $J_{9,12}$=0.3 Hz (para)

Mass spectrum (m/e): 404, 403, 402, 401, 376, 374, 360, 358, 347, 345, 332, 330, 317, 315, 303, 301, 277, 275, 180, 167, 153, 140.

0.2 g of the starting substance, (±)-14-oxo-15-hydroxy-E-homoeburnane-(3α,17α) are recovered from the lower spot.

(b) 1.1 g of ferric chloride hexahydrate are added to a solution of 1.3 1 g (4.01 mmoles) of (±)-14-oxo-15-hydroxy-E-homoeburnane-(3α,17α), melting at 193° C. to 195° C., in 15 ml of glacial acetic acid, and 5 ml of a 1 molar bromine solution in glacial acetic acid are added to the mixture in a single portion at room temperature under constant stirring. The reaction mixture is stirred at room temperature for additional 9 hours, thereafter it is diluted with 200 ml of water, and the pH of the aqueous phase is adjusted to 5 with 25% aqueous ammonia. The mixture is extracted then with 100, 80 and 60 ml of dichloromethane. The organic phases are combined, admixed with 100 ml of water, and the pH of the aqueous phase is adjusted to 10 with 25% aqueous ammonia. The mixture is shaken, the dichloromethane phase is separated, washed thrice with 100 ml of water, each, dried over anhydrous solid magnesium sulfate, filtered, and the filtrate is evaporated to dryness in vacuo. The 1.5 og of dry residue obtained are subjected to preparative thin layer chromatography. Kieselgel PF$_{254+366}$ grade silica gel plates, 20×20 cm in area and 1.55 mm in thickness, are applied as adsorbent, and a 10:3 mixture of benzene and acetonitrile is applied as solvent. The eluted substances are crystallized from methanol. 0.2134 g (13.2%) of (±)-9-bromo-14-oxo-15-hydroxy-E-homoeburnane-(3α,17α) are isolated from the upper spot. This substance (the product with the higher R$_f$value) is identical with the compound of the highest R$_f$ value prepared as described in point (a).

0.6684 g (41.4%) of (±)-11-bromo-14-oxo-15-hydroxy-E-homoeburnane-(3α,17α), a product with lower R$_f$value, are isolated from the middle spot. This substance is identical with the compound of the medium R$_f$value prepared as described in point (a).

9-Bromo-14,15-dioxo-E-homoeburnane-(3α,17α) and 11-bromo-14,15-dioxo-E-homoeburnane-(3α,17α) are also formed in the reaction in an amount of about 5%. These compounds were identified by thin layer chromatography.

PREPARATION EXAMPLE 2

(+)-3(S),17(S)-9-Bromo-14-oxo-15-hydroxy-E-homoeburnane and (+)-3(S),17(S)-11-bromo-14-oxo-15-hydroxy-E-homoeburnane 1.10 g of ferric chloride hexahydrate are added to a solution of 1.45 g (4.02 mmoles) of (+)-3(S),17(S)-14-oxo-15-hydroxy-E-homoeburnane hydrochloride (m.p.: 240° C. to 242° C.; $[\alpha]_D^{20}$=+37.8°, c=1% pyridine) in 15 ml of glacial acetic acid, and 5 ml of a 1 molar bromine solution in glacial acetic acid are added slowly, at a rate of 0.5 ml/min., to the solution at room temperature under constant stirring. When the addition is complete the mixture is stirred for additional 9 hours at room temperature. When the reaction terminates the mixture is diluted with 200 ml of water, and the pH of the mixture is adjusted to 5 with 25% aqueous ammonia. The resulting solution is extracted with 100, 80 and 60 mo of dichloromethane. The organic phases are combined, admixed with 100 ml of water, and the pH of the aqueous phase is adjusted to 10 with 25% aqueous ammonia. The mixture is shaken, the dichloromethane phase is separated, washed thrice with 100 ml of water, each, dried over solid anhydrous magnesium sulfate, filtered, and the filtrate is evaporated in vacuo.

The 1.4 g of dry residue obtained are subjected to preparative thin layer chromatography. Kieselgel PF$_{254+366}$ grade silica gel plates, 20×20 cm in area and 1.5 mm in thickness, are applied as adsorbent, and a 10:3 mixture of benzene and acetonitrile is applied as solvent. The eluted substances are crystallized from methanol.

The substance with the higher R$_f$value is (+)-3(S),-17(S)-9-bromo-14-oxo-15-hydroxy-E-homoeburnane. This compound is obtained with a yield of 0.2 g (12.3%) and melts at 104° C. to 105° C. The empirical formula of the substance is $C_{20}H_{23}BrN_2O_2$ (mol. wt.: 403.33).

IR spectrum (KBr): $v_{max}$ 3380 cm$^{-1}$ (—OH), 1690 cm$^{-1}$ (—CO).

$[\alpha]_D^{20} = +43.7°$ (c=1%, in chloroform).

The substance with the lower $R_f$ value is (+)-3(S),17(S)-11-bromo-14-oxo-15-hydroxy-E-homoeburnane. This compound is obtained with a yield of 0.8 g (49.4%) and melts at 117° C. to 119° C. The empirical formula of the substance is $C_{20}H_{23}BrN_2O_2$ 403.33).

IR spectrum (KBr): $v_{max}$. 3350 cm$^{-1}$ (—OH), 1680 cm$^{-1}$ (—CO).

$[\alpha]_D^{20} = +18.3°$ (c=1%, in chloroform).

The starting materials of the formula (II) where X is halogen in the 10-position of the 14-oxo-15-hydroxy-E-homoeburnane are prepared themselves by treating a racemic or optically active 9-halo-octahydroindoloquinolizine of the formula (IV)

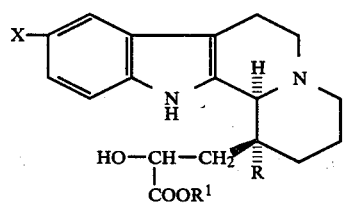

(IV)

wherein R and X are as defined above and $R^1$ is $C_1$ to $C_6$ alkyl, or a pharmaceutically acceptable acid addition salt thereof with a strong base, and if desired, the 15-epimers of the resulting compound having the formula (II) where X is halogen in the 10-position, are separated from each other, and/or, if desired, the resulting substance is converted into its pharmaceutically acceptable acid addition salt and/or resolved.

The compound of the formula (IV) itself can be prepared as follows: A 9-halo-1,2,3,4,6,7-hexahydroindolo[2,3-a]quinolizine is reacted with a 2-acyloxy-acrylic acid ester, and the resulting 1-(2'-acyloxy-2-alkoxycarbomylethyl)-9-halo-1,2,3,4,6,7-hexahydroindolo[2,3-a]quinolizine is first reduced and then deacylated or else is first deacylated and then reduced.

Of the strong bases applicable in the preparation of compounds of the formula (II) from the compounds of the formula (IV), the following are to be mentioned: alkali metal hydrides, such as sodium hydride, alkali metal alcoholates, such as sodium methoxide, sodium ethoxide, sodium tertiary butoxide and potassium tertiary butoxide, alkali metal amides, such as sodium amide and potassium amide, alkali metal dialkylamides, such as lithium diisopropylamide.

The treatment can be performed in an inert aprotic non-polar organic solvent, such as an aromatic hydrocarbon (e.g. benzene, toluene, xylene). The starting substance is treated with an alkali preferably at or close to the boiling point of the solvent used.

The above reaction yields the compound of formula (II) where X is 10-halo as mixtures of 15-epimers. If desired, the individual epimers can be separated from each other preferably by preparative layer chromatography.

It is preferred to use Merck PF$_{254+366}$ grade silica gel plates in the preparative layer chromatography. Various solvent combinations can be utilized as running and eluting agents.

REFERENCE EXAMPLE 3

10-bromo-14-oxo-15-hydroxy-E-homoeburnane-(3α,17α)

0.30 g (2.7 mmoles) of potassium tert.-butoxide are added to a suspension of 3.0 g (6.9 mmoles) of 9-bromo-1α-ethyl-1-(2-hydroxy-2-methoxycarbonyl-ethyl)-1,2,3,4,5,6,7,17-octahydro-12baH-indolo[2,3-a]quinolizine in 200 ml of dry toluene and 2.8 ml (2.6 g) of acetophenone, and the mixture is stirred and refluxed in an argon atmosphere for 4 hours. When the reaction terminates, the mixture is cooled to 0° C. and shaken four times with 30 ml of cold 2.5% aqueous sulfuric acid, each. The aqueous acidic phases are combined, cooled, the pH of the solution is adjusted to 10 with 25% aqueous ammonia, and then extracted three times with 30 ml of dichloromethane, each. The organic phases are combined, dried over magnesium sulfate, filtered, and the filtrate is evaporated in vacuo. The residue is crystallized from 10 ml of methanol to obtain 1.85 g (66.6%) of the named compound as a mixture of epimers; m.p.: 206° C. to 208° C. The empirical formula of the product is $C_{20}H_{23}BrN_2O_2$ (mol. wt.: 403.33).

The epimers are separated from the epimeric mixture by preparative thin layer chromatography. Kieselgel PF$_{254+366}$ grade silica gel plates, 20×20 cm in area and 1.5 mm in thickness, are applied as adsorbent, and a 14:3 mixture of benzene and methanol is utilized as solvent. The product is eluted with dichloromethane. The fast-moving epimer is termed as epimer "A", and the slow-moving epimer is termed as epimer "B". Epimer "A" is crystallized from 5 ml of methanol, and epimer "B" is crystallized from 10 ml of methanol.

0.4 g of epimer "A" are isolated from the upper spot, which corresponds to a yield of 21.6%. The substance melts at 177° C. to 178° C.

IR spectrum (KBr): $v_{max}$. 3400 cm$^{-1}$ (—OH), 1660 cm$^{-1}$ (amide—CO).

Mass spectrum (m/e): 404, 403, 402, 401, 376, 374, 360, 358, 347, 345, 332, 330, 317, 315, 303, 301, 277, 275, 180, 167, 153, 140.

1.25 g of epimer "B" are isolated from the lower spot; i.e. this epimer is obtained with a yield of 67.6%. The substance melts at 214° C. to 216° C.

IR spectrum (KBr): $v_{max}$ 3400 cm$^{-1}$ (—OH), 1685 cm$^{-1}$ (amide—CO).

Mass spectrum (m/e): 404, 403, 402, 401, 376, 374, 360, 358, 347, 345, 332, 330, 303, 301, 277, 275, 180, 167, 153, 140.

NMR spectrum (deuterochloroform): δ0.96 (t, 3H, —CH$_3$), 7.39–8.24 (m, 3H, aromatic protons) ppm. C$_9$—H=7.51 ppm, J$_{12,9}$=0.2 Hz (para); C$_{11}$—H=7.39 ppm, J$_{11,12}$=8.7 Hz (ortho); C$_{12}$—H=8.24 ppm, J$_{11,9}$=2.8 Hz (meta).

What we claim is:

1. A process for the preparation of a halovincamone of the formula (I)

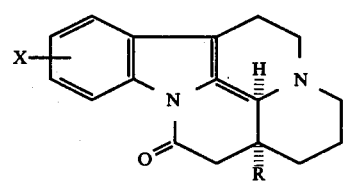

wherein

R is a $C_1$ to $C_6$ alkyl group and X is halogen, or an optically active isomer or a pharmaceutically acceptable acid addition salt thereof, which comprises oxidizing at a temperature of 40° to 140° C. a single epimer or an epimer mixture of a racemic or optically active halogenated 14-oxo-15-hydroxy-E-homoeburnane of the formula (II)

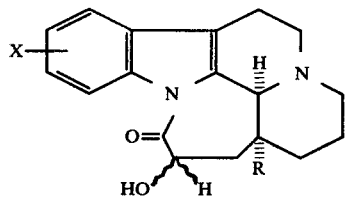

or a pharmaceutically acceptable acid addition salt thereof with manganese dioxide precipitated onto an inert support with a large surface area, and if desired, the resulting compound of the formula (I) is converted into a pharmaceutically acceptable acid addition salt thereof and/or resolved.

* * * * *